United States Patent
Esser et al.

(10) Patent No.: US 10,393,570 B2
(45) Date of Patent: Aug. 27, 2019

(54) PRECISION SCALE HAVING A REMOVABLE CLIMATE MODULE

(71) Applicant: Sartorius Lab Instruments GmbH & Co. KG, Goettingen (DE)

(72) Inventors: Richard Esser, Bovenden-Eddigehausen (DE); Heyko Holst, Goettingen (DE); Sigo Muehlich, Bovenden (DE); Falko Hilbrunner, Ilmenau (DE); Thomas Fehling, Witzenhausen (DE); Benno Gatzemeier, Goettingen (DE); Rainer Gunkel, Schimberg (DE)

(73) Assignee: SARTORIUS LAB INSTRUMENTS GMBH & CO. KG, Goettingen (DE)

( * ) Notice: Subject to any disclaimer, the term of this patent is extended or adjusted under 35 U.S.C. 154(b) by 346 days.

(21) Appl. No.: 15/149,926

(22) Filed: May 9, 2016

(65) Prior Publication Data

US 2016/0252389 A1    Sep. 1, 2016

Related U.S. Application Data

(63) Continuation of application No. PCT/EP2014/002365, filed on Sep. 2, 2014.

(30) Foreign Application Priority Data

Nov. 8, 2013 (DE) .......................... 10 2013 018 767
Feb. 7, 2014 (DE) .......................... 10 2014 101 558

(51) Int. Cl.
*G01G 21/28* (2006.01)
*G01G 23/01* (2006.01)
(Continued)

(52) U.S. Cl.
CPC .............. *G01G 23/01* (2013.01); *B01L 3/021* (2013.01); *G01G 17/04* (2013.01); *G01G 19/303* (2013.01);
(Continued)

(58) Field of Classification Search
CPC ....... G01G 23/01; G01G 17/04; G01G 19/303; G01G 21/22; G01G 21/286; G01G 23/48;
(Continued)

(56) References Cited

U.S. PATENT DOCUMENTS 4,858,161 A    8/1989  Baumann
6,557,391 B2 *  5/2003  Luchinger .............. G01G 21/22
                                                      177/50
(Continued)

FOREIGN PATENT DOCUMENTS

DE      3714540 C2    8/1996
DE     29912867 U1    3/2000
(Continued)

OTHER PUBLICATIONS

Computer translation of DE 299 12 867 from the EPO website, downloaded Aug. 29, 2018.*
(Continued)

*Primary Examiner* — Randy W Gibson
(74) *Attorney, Agent, or Firm* — Edell, Shapiro & Finnan, LLC

(57) ABSTRACT

A precision balance including a weighing chamber (16); a draft shield (18, 20, 22), which surrounds the weighing chamber (16); a climate module (34), which is detachably disposed in the weighing chamber (16); a processor (32) and a data input unit, which both form part of the overall precision balance; and a data transmission path, over which data is exchanged between the climate module (34) and the processor (32). Also disclosed is a climate module for a (Continued)

precision balance. The climate module (34) forms a self-contained modular unit and includes an air pressure sensor (62), an air humidity sensor (54) and an air temperature sensor (52) The climate module also includes a data transmission path configured to transmit data to a processor external to the climate module, and a mounting mechanism configured to secure the climate module detachably to a weighing module (10).

8 Claims, 2 Drawing Sheets

(51) Int. Cl.
*G01G 23/48* (2006.01)
*G01N 9/26* (2006.01)
*G05D 11/00* (2006.01)
*B01L 3/02* (2006.01)
*H01L 21/67* (2006.01)
*G01G 17/04* (2006.01)
*G01G 19/30* (2006.01)
*G01G 21/22* (2006.01)

(52) U.S. Cl.
CPC ........... *G01G 21/22* (2013.01); *G01G 21/286* (2013.01); *G01G 23/48* (2013.01); *G01N 9/26* (2013.01); *G05D 11/00* (2013.01); *H01L 21/67* (2013.01)

(58) Field of Classification Search
CPC .......... B01L 3/021; G01N 9/26; G05D 11/00; H01L 21/67
See application file for complete search history.

(56) References Cited

U.S. PATENT DOCUMENTS

| | | | | |
|---|---|---|---|---|
| 7,423,226 | B2* | 9/2008 | Rotach | G01G 23/30 177/180 |
| 7,829,800 | B2* | 11/2010 | Thiel | G01G 17/06 177/180 |
| 8,683,880 | B2* | 4/2014 | Wilby | G01G 9/00 177/180 |
| 2007/0175675 | A1* | 8/2007 | Nufer | G01G 21/286 177/180 |
| 2010/0089152 | A1* | 4/2010 | Kolada | G01F 19/00 73/426 |
| 2010/0285614 | A1* | 11/2010 | Wilby | G01G 9/00 438/14 |
| 2013/0328842 | A1* | 12/2013 | Barnhoefer | G09G 3/3406 345/207 |
| 2016/0252388 | A1* | 9/2016 | Esser | G01G 17/04 177/1 |

FOREIGN PATENT DOCUMENTS

| | | | |
|---|---|---|---|
| EP | 1975577 A1 | 10/2008 | |
| WO | WO 02/03449 A2 * | 1/2002 | ........... H01L 21/66 |

OTHER PUBLICATIONS

International Search Report in counterpart International Application No. PCT/EP2014/002365, dated Nov. 17, 2014.
International Preliminary Report on Patentability in counterpart International Application No. PCT/US2014/002365, dated May 12, 2016, 7 pages.

* cited by examiner

PRECISION SCALE HAVING A REMOVABLE CLIMATE MODULE

CROSS-REFERENCE TO RELATED APPLICATIONS

This is a Continuation of International Application PCT/EP2014/002365, which has an international filing date of Sep. 2, 2014, and the disclosure of which is incorporated in its entirety into the present Continuation by reference. The following disclosure is also based on and claims the benefit of and priority under 35 U.S.C. § 119(a) to German Patent Application Nos. DE 10 2013 018 767.2, filed Nov. 8, 2013, and to DE 10 2014 101 558.4, filed Feb. 7, 2014, which are also incorporated in their respective entireties into the present Continuation by reference.

FIELD OF THE INVENTION

The invention relates to a precision balance, thus, a high resolution electronic balance with a removable climate module.

BACKGROUND

In high resolution balances the air buoyancy, to which the sample to be weighed is subject, has an effect on the accuracy of the measurement results. Therefore, for measurements of ultra high accuracy it is necessary to determine the air density in order to determine an air buoyancy factor. For precision balances it is known, for example, that the air buoyancy correction factor is determined by a comparison measurement of two reference objects having a mass and density that are already known beforehand.

It is also known that the temperature, the air pressure and the humidity also affect the balance itself, in particular, the load cell. For this reason, in order to compensate for the variances in the balance display with changing ambient parameters, correction factors are stored in the device, for example, in the form of curves or tables. In addition, temperature and air humidity sensors are disposed, in particular, in the surrounding area of the load cell. Then these temperature and air humidity sensors are used to automatically correct the balance itself, as a function of the changing ambient conditions, also called climate changes.

Thus, the German patent DE 37 14 540 C2 describes a method for automatically calibrating a high resolution electronic balance, wherein such environmental factors as the temperature change and the humidity change, both of which are detected from the outside, are used to calibrate the balance itself. The corresponding calibration factor is determined by a computer and corrects the weighing result.

The German patent DE 299 12 867 U1 discloses an analytical balance with a measuring sensor for ambient parameters. In this case the analytical balance has a display that is provided on the rear wall of the weighing chamber. The display shows the temperature in the weighing chamber and the air humidity in the weighing chamber as well as in general the air pressure that is usually present. In this case it is assumed that, when the air is wet, the surface of the sample to be weighed will be covered with moisture, which is a function of the variances in the air humidity. Therefore, the operator is informed by the display that, for example, with changing air humidity, the sample to be weighed should remain in the weighing chamber longer, in order to obtain a stable end value of the surface moisture. If there are extreme fluctuations in the air pressure, then the operator can perform a so-called buoyancy correction by feeding the displayed data to a processor in the balance via an input unit. With respect to the temperature, this temperature is used to determine the deviation from the reference temperature and to consider corresponding correction factors.

Finally there are also climatized measuring chambers, in which there are precision balances, into which the climate data of the measuring chamber are entered. The climate data from the climate module or the sensors thereof are fed manually or automatically into the balance.

SUMMARY

An object of the present invention is to provide a precision balance that is compact and that ensures an improved measuring accuracy with less complexity.

This object, according to one formulation of the invention, is achieved with a precision balance, comprising a weighing chamber; a draft shield, which surrounds the weighing chamber; a climate module, which includes an air pressure sensor, an air humidity sensor and an air temperature sensor and which is disposed in the weighing chamber in such a way that it can be removed; a processor; a data input unit; and a data transmission path, over which data can be exchanged between the climate module and the processor. The object, according to a further formulation, is achieved with a climate module configured to electrically couple to a precision balance in a detachable manner, wherein the climate module forms a self-contained modular unit and comprises an air pressure sensor, an air humidity sensor and an air temperature sensor, as well as a data transmission path, over which data can be sent to a processor external to the climate module.

The invention makes use of the idea of combining all of the components and functions, which are necessary for compensating for the climate changes in the weighing results, in the precision balance. Therefore, no external computers, sensors, etc. are necessary. Instead, the user can be provided with a compact measurement laboratory, which can be used as a mobile unit because there is no need to take along any external sensors, computers, etc. Since the climate module is interchangeable (i.e., can be detached from the balance without destroying it), it can be sent, if desired, to an external institute or service provider for calibration. In the meantime the precision balance can still be used by installing a replacement climate module. As a result, it is possible to have on a rolling basis one or (in the case of several precision balances) a plurality of climate modules being calibrated, while measuring with the other climate modules.

The climate module offers an additional advantage that older balances can be retrofitted. The only requirement for such a retrofitting is, in addition to the data transmission path, the software of the processor.

In terms of accuracy the precision balance of the invention has the advantage that the climate data are measured behind the draft shield (and not just in the chamber, in which the balance is located). Therefore, precisely the air density that is relevant to the buoyancy is determined. In addition, since the climate data are transmitted automatically to the processor, transmission errors can be virtually eliminated. According to the German patent DE 299 12 867 U1, such transmission errors are possible, for example, when transferring values from the so-called calibration certificate into the calibration software, or when reading in the climate data of the external sensors.

According to one embodiment, it is provided that the climate module is connected to the processor via an electrical plug-in connection. The plug-in connection can be integrated into a mechanical receptacle, which is used to attach the climate module to the precision balance. In this way the data transmission path to the processor is automatically established, when the climate module is installed inside the draft shield.

According to an alternative embodiment, it is provided that the climate module is coupled to the processor over a wireless transmission. In this case the climate module can be disposed at any location inside the draft shield, for example, on a partition wall, where it will interfere the least, without having to take into consideration whether a plug-in connection can be arranged at this location in such a way that it is useful. In addition, the absence of a plug-in connection has the advantageous effect that the interior of the weighing compartment can be designed to be smoother and, therefore, easier to clean.

Preferably the climate module includes an air pressure sensor, an air humidity sensor and an air temperature sensor. These sensors can be used to record the climate data that are essential for a precise measurement.

In addition, it can be provided that inside of the climate module there is a sensor that is designed to determine the degree of ionization in the weighing chamber and that is coupled to the data transmission path. As a result, an additional parameter can be determined and taken into account in the correction of the weighing result. The processor generates, as a function of the degree of ionization that is determined, an output signal, for example, to actively change the degree of ionization, by using an ionization device, which is activated after reaching the degrees of ionization that are determined. Furthermore, a display can also indicate to the user that the degree of ionization inside the weighing chamber is too high and should be discharged.

It can also be provided that the climate module has a light sensor, which is coupled to the data transmission path. Such an arrangement allows another parameter to be determined and taken into account in correcting the weighing result. The processor can output an output signal following a specified level of incident light. As a result, it is possible to determine the effect of the incident light on the weighing process, so that appropriate steps can be taken in the process itself. The output signal can also be an indicator.

According to one embodiment, it is provided that the processor is designed such that it uses the air pressure, the air humidity and the air temperature in the weighing chamber to determine, based on the density of the sample to be weighed, the air buoyancy of at least one test sample as well as to determine the buoyancy correction factor. This arrangement makes it possible to obtain from the climate module the meteorologically traceable values in sync with the download of the mass value, with which the processor is able to correct the weighing result.

According to one embodiment, an electronic memory, in particular, an EEPROM, which can be read out by an external reader and in which the calibration values and the correction values for the climate module can be stored, is provided inside the climate module. In order to make adjustments, the calibration values can be stored in an electronic memory on the climate module, in particular, can be stored in an EEPROM. This is done at an external service provider. If the climate module is then reconnected to the precision balance, these data are then immediately available to the processor of the balance. In addition, the memory can be used to store, among other things, at least some of the following sensor calibration data: the number of the calibration certificate, the current calibration values, the calibration date, the name of the calibration laboratory, the name of the person in charge and the calibration history. In addition, so-called uncertainty values can also be stored for each climate variable in the memory of the climate module, so that, for example, in order to compute the air density, the computation of the uncertainty of the air density can also be performed by the precision balance.

According to one embodiment, it is provided that the climate module can also be used as a stand-alone unit external to a balance and can be connected to a USB port of a PC via an I²C bus. This arrangement makes it easier to perform an external calibration. In addition, the climate module can be used in other applications to record climate variables without having to be connected to a balance. For this purpose the printed circuit board of the climate module can easily have a plug-in extension, in order to be connected to a USB adapter.

BRIEF DESCRIPTION OF THE DRAWINGS

Additional features and advantages of the invention will become apparent from the following description and from the following drawings, to which reference is made. The drawings show in.

DETAILED DESCRIPTION

Figure 1:
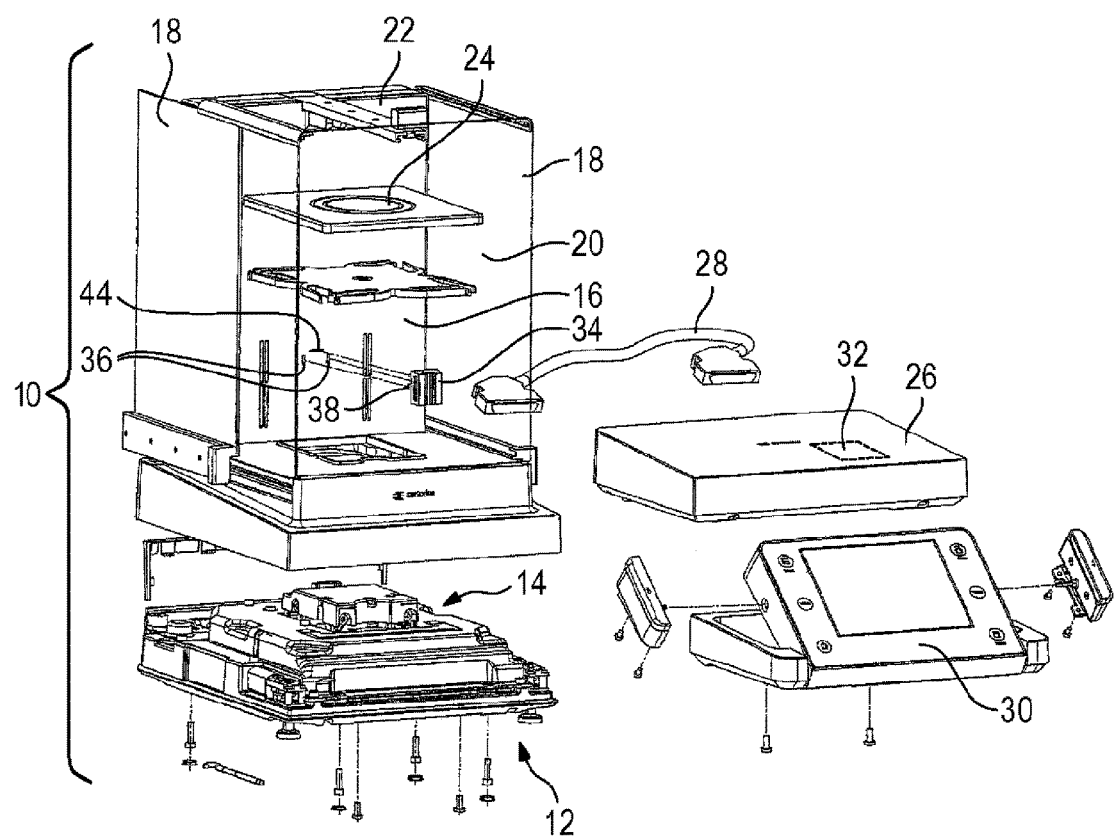
FIG. 1 an exploded view of a precision balance, according to the invention.

FIG. 1 shows a high resolution electronic balance (precision balance) that in this exemplary embodiment permits mass comparisons to be performed for the accuracy classes E1-F2 in compliance with OIML R 111-1.

However, the invention relates, in general, to any high resolution electronic balance of high accuracy, i.e., with a measuring resolution in the range of micrograms down to nanograms.

The precision balance comprises a load cell 14 with a base 12. In addition, the load cell 14 comprises a weighing chamber 16, which is formed by a draft shield with adjustable side walls 18, a front wall 20 and a rear wall 22. The weighing chamber 16 is separated from the surrounding area by the draft shield. A weighing dish 24 is used to hold the sample to be weighed. These components together form a weighing module 10.

An electronic evaluation system 26, which is designed as a separate part in this embodiment, is electronically coupled to the load cell 14 via a cable 28. A display unit 30, which is coupled to the evaluation system 26, is used both as a display and as a data input unit. While the electronic evaluation system 26 and the display 30 are embodied as components physically separated from the weighing module 10 in the illustrated embodiment, other embodiments can incorporate one or both of these components 26 and 30 into the weighing module 10.

The electronic evaluation system 26 houses, among other things, a processor 32, which receives data from the load cell 14.

The weighing chamber 16 has a climate module 34, which is designed as a structurally separate unit and which can be mechanically coupled to the rear wall 22 through a disconnectable plug-in connection (hence, is attached in a manner allowing the climate module to be disconnected without destroying it), and, in particular, preferably without the aid of a tool.

For this purpose the rear wall 22 has two slots 36, which are spaced apart from each other and in which flexible locking hooks 38 (see also FIG. 2) engage with the outer housing 40 of the climate module.

Figure 2:
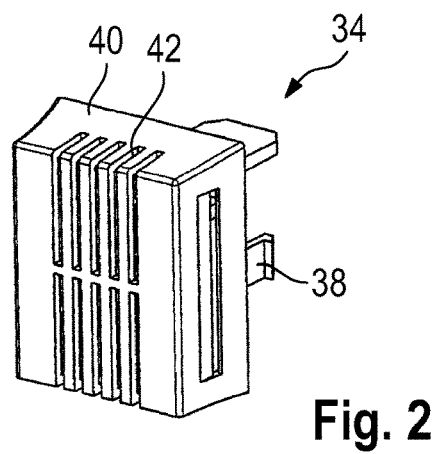
FIG. 2 a perspective view of an inventive climate module, which can be used in the precision balance of the invention, FIG. 3 a side view of the climate module from FIG. 2 without the outer housing, and FIG. 4 a plan view of the climate module from FIG. 2, also without the outer housing.
Figure 3:
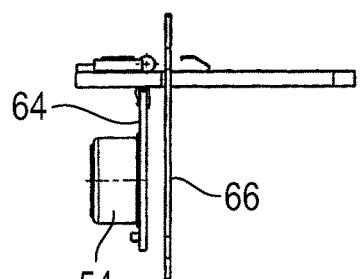
Figure 4:
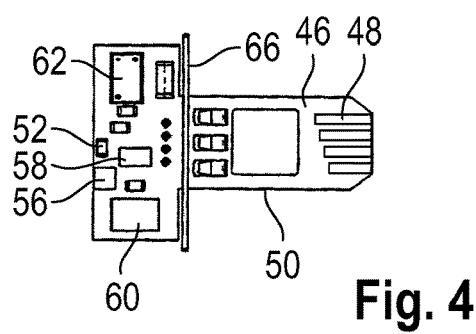

FIGS. 2 to 4 show the climate module 34 in more detail.

The outer housing 40 has a number of apertures 42, through which the interior of the outer housing 40 changes over into the weighing chamber 16 and becomes a part of the weighing chamber 16, so that the climate inside the weighing chamber 16 corresponds to the climate inside the outer housing 40.

The climate module 34 is electronically coupled via an electrical plug-in connection to a corresponding plug receptacle 44 in the rear wall 22. The plug receptacle 44 is electrically connected to the processor 32. A plug 46 with contacts 48 is plugged into the plug receptacle 44 on the climate module 34. As a result, the plug 46 forms a module-sided part of the electrical plug-in connection.

As an alternative to an electrical plug-in connection, a wireless transmission, such as WLAN or Bluetooth, can be used.

The electrical plug-in connection (or the wireless transmission used as an alternative) forms a data transmission path, over which the data can be transferred from the climate module 34 to the processor 32 and, if desired, can be transferred back to the climate module.

The plug 46 is preferably a section of a circuit board 50, on which a plurality of sensors for detecting the climate in the weighing chamber 16 are disposed. Therefore, an air temperature sensor 52, an air humidity sensor 54, a light sensor 56, which is arranged directly in the vicinity of an aperture 42, and a sensor 58 for detecting the degree of ionization in the weighing chamber 16 are provided on the circuit board 50, and an electronic memory 60 is also provided on the circuit board. An air pressure sensor 62 is mechanically and electrically coupled to the circuit board 50 with a bracket 64.

A plurality of the sensors can also be combined into combined sensors.

A wall 66 closes the shell-like outer housing 40, so that the narrow tongue-like section of the circuit board 50, which is located to the right of the wall 66 in FIG. 4, can be inserted into the rear wall 22 and the plug receptacle 44.

Each sensor is coupled to the processor 32 via corresponding contacts 48. Similarly the memory 60 is coupled to the processor 32. During the weighing operation the density of the sample to be weighed can be entered into the precision balance, for example, using the display unit 30, which is also used simultaneously as a data input unit by way of, for example, the touch screen. As an alternative, the density of the sample to be weighed can have already been stored.

Then a sample to be weighed is placed on the weighing dish 24.

The air pressure, the air humidity and the air temperature are determined by the sensors 62, 54 and 52, respectively; and the corresponding data are then transmitted to the processor 32.

The air density is determined in the processor 32. The input densities are used in the processor to determine the air buoyancy correction factor and/or the air buoyancy of the sample to be weighed, as a function of the air pressure, the air humidity, the air temperature as well as the density of the sample to be weighed; and the conventional weighing result of the sample to be weighed, i.e., the mass of the sample to be weighed that is corrected by its air buoyancy, is determined and displayed in the display unit 30.

In addition, the weighing value of the sample to be weighed can be corrected via additional parameters, for example, by a known effect of the varying air humidities or temperatures on the weighing result. This feature permits the accuracy of the weighing result to be even higher.

In addition, the calibration values and the correction values for the climate module 34, which had been input during the calibration of the climate module 34, are stored in the memory 60.

This calibration is performed outside of the precision balance. To this end the climate module 34 is simply unplugged from the weighing chamber 16 without having to disconnect a wire connection. Then the climate module 34 is sent to an appropriate calibration institute that stores the number of the calibration certificate, i.e., the new calibration values, the calibration date, the name of the calibration laboratory, the name of the person in charge and the calibration history, in the memory 60. These values are read out later by the application program, when the climate module 34 is once again in the precision balance, and flow directly into the computation. Even the values of the light sensor 56 and the sensor 58 for determining the degree of ionization in the weighing chamber 16 are determined.

For example, when the level of incident light increases, a corresponding signal will be shown on the display that, for example, the measurement is uncertain due to increased exposure to sunlight and, thus, due to a temperature change in the weighing chamber. As a result, the processor sends an output signal as a function of the exposure to incident light. As soon as the degree of ionization is too high, an ionization device is activated; and this ionization device ionizes the air in the weighing chamber and makes sure that the sample to be weighed is discharged, or a warning about an excessive charge of the sample to be weighed is sent.

The memory 60 is preferably an EEPROM.

In addition, the connection between the climate module 34 and the rest of the precision balance is implemented using an I²C bus.

The climate module 34 can be connected to a computer via a USB adapter, into which the climate module is inserted, in order to calibrate the sensors 52 to 58 and 62 without having to connect the climate module 34 to the weighing module 10.

As can be seen, the climate module is designed so that it can also be used as a stand-alone unit external to a balance and can be connected to a USB port of a PC using an I²C bus.

LIST OF REFERENCE NUMERALS 10 weighing module
12 base
14 load cell
16 weighing chamber
18 side wall
20 front wall
22 rear wall
24 weighing dish
26 evaluation system
28 cable
30 display unit
32 processor
34 climate module
36 slots 38 locking hooks
42 apertures
46 plug
48 contacts
50 printed circuit board
52 air temperature sensor
54 air humidity sensor
56 light sensor
58 sensor
60 memory
62 air pressure sensor
64 bracket
66 wall

What is claimed is:

1. Precision balance, comprising:
   a weighing chamber;
   a draft shield, which surrounds the weighing chamber and which comprises a mechanically resilient shield coupling part;
   a climate module, which comprises an air pressure sensor, an air humidity sensor and an air temperature sensor, and which further comprises a mechanically resilient module coupling part configured complementary to the shield coupling part,
      wherein the climate module is configured to be mounted and dismounted in the weighing chamber by attaching to and detaching from the draft shield via the coupling parts;
   a processor;
   a data input unit; and
   a data transmission path, over which data is exchanged between the climate module and the processor.

2. The precision balance as claimed in claim 1, wherein the data transmission path comprises an electrical plug-in connection.

3. The precision balance as claimed in claim 1, wherein the data transmission path comprises a wireless transmission.

4. The precision balance as claimed in claim 1, wherein the climate module further comprises a sensor coupled to the data transmission path and configured to determine a degree of ionization in the weighing chamber.

5. The precision balance as claimed in claim 1, wherein the climate module comprises a light sensor, which is coupled to the data transmission path.

6. The precision balance as claimed in claim 1, wherein the processor is programmed to determine, based on a density of a substance to be weighed, an air buoyancy of a test sample or a buoyancy correction factor from the air pressure, the air humidity and the air temperature in the weighing chamber.

7. The precision balance as claimed in claim 1, wherein the shield coupling part comprises at least one slot in a wall of the draft shield and the module coupling part comprises at least one locking protrusion.

8. The precision balance as claimed in claim 7, wherein the shield coupling part comprises at least two mutually spaced slots in the wall of the draft shield and the module coupling part comprises at least two mutually spaced locking tabs configured to insert respectively into the at least two slots.

* * * * *